(12) United States Patent
Harper et al.

(10) Patent No.: US 8,080,654 B2
(45) Date of Patent: Dec. 20, 2011

(54) MACROCYCLIC QUINOXALINE COMPOUNDS AS HCV NS3 PROTEASE INHIBITORS

(75) Inventors: Steven Harper, Pomezia (IT); Vincenzo Summa, Pomezia (IT); Nigel J. Liverton, Harleysville, PA (US); John A. McCauley, Maple Glen, PA (US)

(73) Assignees: Insituto di Ricerche di Biologia Molecolare P. Angeletti SpA, Rome (IT); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/112,281

(22) Filed: May 20, 2011

(65) Prior Publication Data
US 2011/0224134 A1    Sep. 15, 2011

Related U.S. Application Data

(63) Continuation of application No. 12/504,955, filed on Jul. 17, 2009, now Pat. No. 7,973,040.

(60) Provisional application No. 61/135,559, filed on Jul. 22, 2008.

(51) Int. Cl.
*C07D 498/08* (2006.01)
(52) U.S. Cl. .................................................. 540/457
(58) Field of Classification Search .................. 540/457
See application file for complete search history.

(56) References Cited

U.S. PATENT DOCUMENTS

| | | | |
|---|---|---|---|
| 3,480,613 | A | 11/1969 | Walton |
| 6,323,180 | B1 | 11/2001 | Llinas-Brunet et al. |
| 6,608,027 | B1 | 8/2003 | Tsantrizos et al. |
| 6,777,395 | B2 | 8/2004 | Bhat et al. |
| 6,955,174 | B2 | 10/2005 | Friedrichs et al. |
| 7,470,664 | B2 | 12/2008 | Holloway et al. |
| 2002/0019363 | A1 | 2/2002 | Ismaili et al. |
| 2002/0107138 | A1 | 8/2002 | Hoveyda et al. |
| 2003/0236216 | A1 | 12/2003 | Devos et al. |
| 2004/0006007 | A1 | 1/2004 | Gosselin et al. |
| 2004/0063658 | A1 | 4/2004 | Roberts et al. |
| 2004/0067901 | A1 | 4/2004 | Bhat et al. |
| 2004/0229776 | A1 | 11/2004 | Chen et al. |
| 2004/0229818 | A1 | 11/2004 | Llinas-Brunet et al. |
| 2004/0254159 | A1 | 12/2004 | Hasvold et al. |
| 2004/0266668 | A1 | 12/2004 | Nakajima et al. |
| 2005/0020503 | A1 | 1/2005 | Llinas-Brunet et al. |
| 2005/0038240 | A1 | 2/2005 | Connolly et al. |
| 2006/0257980 | A1 | 11/2006 | Li |
| 2007/0027071 | A1 | 2/2007 | Holloway et al. |
| 2010/0099695 | A1 | 4/2010 | Liverton et al. |

FOREIGN PATENT DOCUMENTS

| | | | |
|---|---|---|---|
| EP | 1719773 | A1 | 11/2006 |
| GB | 2337262 | A | 11/1999 |
| GB | 2430621 | A | 4/2007 |
| WO | 97/41211 | A1 | 11/1997 |
| WO | 98/22496 | A2 | 5/1998 |
| WO | 98/46630 | A1 | 10/1998 |
| WO | 99/07733 | A2 | 2/1999 |
| WO | 99/07734 | A2 | 2/1999 |
| WO | 99/38888 | A1 | 8/1999 |
| WO | 99/43691 | A1 | 9/1999 |
| WO | 99/50230 | A1 | 10/1999 |
| WO | 99/64442 | A1 | 12/1999 |
| WO | 00/09543 | A2 | 2/2000 |
| WO | 00/09546 | A2 | 2/2000 |
| WO | 00/25780 | A1 | 5/2000 |
| WO | 00/59929 | A1 | 10/2000 |
| WO | 01/00622 | A1 | 1/2001 |
| WO | 01/47883 | A1 | 7/2001 |
| WO | 01/60379 | A1 | 8/2001 |
| WO | 01/68663 | A1 | 9/2001 |
| WO | 01/77091 | A2 | 10/2001 |
| WO | 01/77113 | A2 | 10/2001 |
| WO | 01/79246 | A2 | 10/2001 |
| WO | 01/90121 | A2 | 11/2001 |

(Continued)

OTHER PUBLICATIONS

Brian W. Dymock et al., "Novel Approaches to the Treatment of Hepatitis C Virus Infection," 11 Antiviral Chemistry & Chemotherapy 79-96 (2000). Hugo R. Rosen & David R. Gretch, "Hepatitis C virus: current understanding and prospects for future therapies," 5 Molec. Med. Today 393-99 (1999).

Darius Moradpour & Hubert E. Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

(Continued)

*Primary Examiner* — Bruck Kifle
(74) *Attorney, Agent, or Firm* — Julie M. Lake; Sheldon O. Heber

(57) ABSTRACT

The present invention relates to macrocyclic a compound of formula (I) and its use as inhibitors of the hepatitis C virus (HCV) NS3 protease, and in treating or preventing HCV infections.

8 Claims, No Drawings

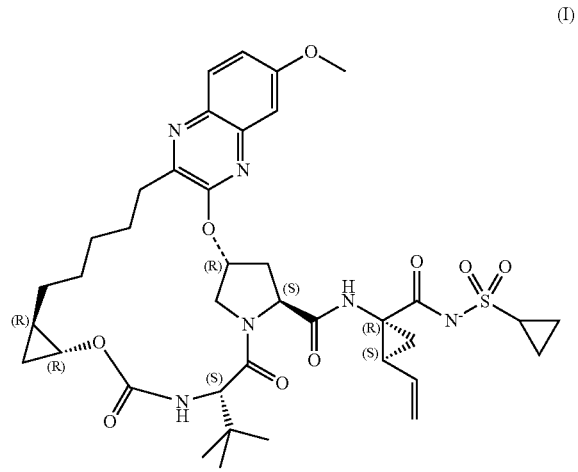

(I)

FOREIGN PATENT DOCUMENTS

| | | |
|---|---|---|
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A1 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 04/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/002924 A2 | 1/2008 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |
| WO | 2010/011566 A1 | 1/2010 |

OTHER PUBLICATIONS

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).
Brain W. Dymock, "Emerging therapies for hepatitis C virus infection," 6 Emerging Drugs 13-42 (2001).
Charlene Crabb, Infectious Diseases. "Hard-Won Advances Spark Excitement about Hepatitis C," Science 506-507 (2001).
Rogers E. Harry-O'Kuru et al., "A Short, Flexible Route toward 2'-C-Branched Ribonucleosides," 62 J. Org. Chem. 1754-59 (1997).
Michael S. Wolfe & Rogers E. Harry-O'Kuru, "A Concise Synthesis of 2'-C-Methylribonucleosides," 36(42) Tetrahedron Letters 7611-14 (1995).
Scott J. Miller et al., "Application of Ring-Closing Metathesis to the Synthesis of Rigidified Amino Acids and Peptides," 118 J. Am. Chem. Soc. 9606-14 (1996).
Jason S. Kingsbury et al., "A Recyclable Ru-Based Metathesis Catalyst," 121 J. Am. Chem. Soc. 791-99 (1999).
Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).
Alois Furstner et al., "Total Synthesis and Structural Refinement of the Cyclic Tripyrrole Pigment Nonylprodigiosin," 64 J. Org. Chem. 8275-80 (1999).
Tina M. Trnka & Robert H. Grubbs, "The Development of L2X2R-CHR Olefin Metathesis Catalysts: An Organometallic Success Story," 34 Acc. Chem. Res. 18-29 (2001).
A. Srikrishna et al., "Enantiospecific Construction of the BC-ring System of Taxanes," 45 Tetrahedron Letters 2939-42 (2004).
Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).
Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).
Paola Conti et al., "Chemoenzymatic Synthesis of the Enantiomers of Desoxymuscarine," 9 Tetrahedron: Asymmetry 657-65 (1998).
Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).
D. Becker & N. Haddad, "Steric Effects in Intramolecular [2+2] Photocycloaddition of C=C Double Bonds to Cyclohexenones," 49(4) Tetrahedron 947-64 (1993).
Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).
Masao Tokuda et al., "Aminyl Radical Cyclization by Means of Anodic Oxidation. Stereoselective Synthesis of cis-1- Methyl-2,5-Disubstituted Pyrrolidines," 26(49) Tetrahedron Letters 6085-88 (1985).
Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).
Herbert O. House et al., "Cyclization of Unsaturated Hydroxylamine Derivatives," 41(5) J. Org. Chem. 855-63 (1976).
Theophil Eicher et al., "Bryophyte Constituents; 7: New Synthesis of (+)-Rosmarinic Acid and Related Compounds," Synthesis 755-62 (Jun. 1996).
Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).
Marc-Andre Poupart et al., "Solid-Phase Synthesis of Peptidomimetic Inhibitors for the Hepatitis C Virus NS3 Protease," 66(14) J. Org. Chem. 4743-51 (2001).
Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).
Anthony C. Allison & Elsie M. Eugui, "Immunosuppressive and other anti-rheumatic activities of mycophenolate mofetil," 44 Agents and Actions Supplements 165-88 (1993).
Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

International Preliminary Report on Patentability and Written Opinion mailed Feb. 3, 2011 in International Application No. PCT/US2009/050915.

MACROCYCLIC QUINOXALINE COMPOUNDS AS HCV NS3 PROTEASE INHIBITORS

CROSS-REFERENCE TO RELATED APPLICATIONS

This application is a Continuation of U.S. patent application Ser. No. 12/504,955, filed Jul. 17, 2009 now U.S. Pat. No. 7,973,040, which claims benefit of priority to U.S. Provisional Patent Application No. 61/135,559, filed Jul. 22, 2008.

FIELD OF THE INVENTION

The present invention relates to macrocyclic compounds that are useful as inhibitors of the hepatitis C virus (HCV) NS3 protease, the synthesis of such compounds, and the use of such compounds for treating HCV infection and/or reducing the likelihood or severity of HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein. NS4A provide a cofactor for NS3 activity.

Potential treatments for HCV infection have been discussed in the different references including Balsano, *Mini Rev. Med. Chem.* 8(4):307-318, 2008, Rönn et al., *Current Topics in Medicinal Chemistry* 8:533-562, 2008, Sheldon et al., *Expert Opin. Investig. Drugs* 16(8):1171-1181, 2007, and De Francesco et al., *Antiviral Research* 58:1-16, 2003.

SUMMARY OF THE INVENTION

The present invention relates to a macrocyclic compound of formula (I) and pharmaceutically acceptable salts thereof. The compound and its salts are HCV NS3 protease inhibitors. The compound and its salts have therapeutic and research applications.

Thus, a first aspect of the present invention describes a compound of formula (I), or a pharmaceutically acceptable salt thereof:

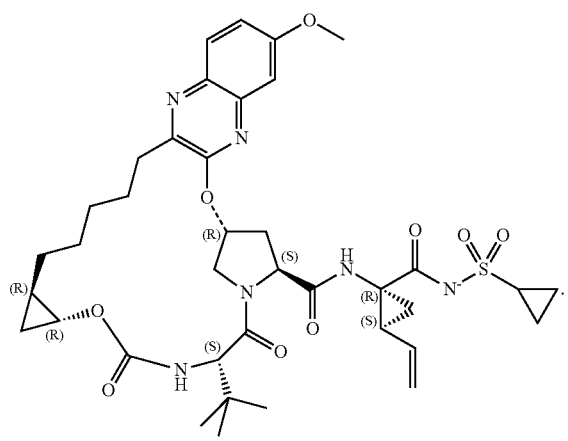

(I)

The present invention also includes pharmaceutical compositions containing a compound of the present invention and methods of preparing such pharmaceutical compositions. The present invention further includes methods of treating or reducing the likelihood or severity of HCV infection.

Other embodiments, aspects and features of the present invention are either further described in or will be apparent from the ensuing description, examples and appended claims.

DETAILED DESCRIPTION OF THE INVENTION

The present invention includes a compound of formula (I), and pharmaceutically acceptable salts thereof. The compound and its pharmaceutically acceptable salts are useful in the inhibition of HCV NS3 protease, the treatment of HCV infection and/or the reduction of the likelihood or severity of an HCV infection. Prophylactic applications include, for example, treatment after suspected past exposure to HCV by such means as blood transfusion, exchange of body fluids, bites, accidental needle stick, or exposure to patient blood during surgery.

As pharmaceutical composition ingredients, the compound and salts may be the primary active therapeutic agent. When appropriate, the compound may be combined with other therapeutic agents including but not limited to other HCV antivirals, anti-infectives, immunomodulators, antibiotics or vaccines.

NS3 inhibitors are also useful in the preparation and execution of screening assays for antiviral compounds. For example, such compounds can be used to isolate enzyme mutants, which are excellent screening tools for more powerful antiviral compounds. Furthermore, the compounds may be used to establish or determine the binding site of other antivirals to HCV protease, e.g., by competitive inhibition.

As further described in Example 2, the formula (I) compound was compared to the compound of Examples 110 and 118 of WO 2008/057209, and has several advantages. WO 2008/057209 is not admitted to be prior art to the claimed invention.

I. Compositions and Methods

Different embodiments include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a compound of formula (I) and (ii) a second therapeutic agent selected from the group consisting of HCV antiviral agents, immunomodulators, and anti-infective agents; wherein the compound of formula (I) and the second therapeutic agent are each employed in an amount that renders the combination effective for inhibiting HCV NS3 protease, or for treating HCV infection and/or reducing the likelihood or severity of HCV infection.

(e) The combination of (d), wherein the HCV antiviral agent is an antiviral selected from the group consisting of HCV protease inhibitors and HCV NS5B polymerase inhibitors.

(f) A method of inhibiting HCV NS3 protease in a subject in need thereof, which comprises administering to the subject an effective amount of a compound of formula (I).

(g) A method of treating HCV infection and/or reducing the likelihood or severity of HCV infection in a subject in need thereof, which comprises administering to the subject an effective amount of a compound of formula (I).

(h) The method of (g), wherein the compound of formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV NS3 protease in a subject in need thereof, which comprises administering to the subject the pharmaceutical composition of (a), (b), or (c) or the combination of (d) or (e).

(k) A method of treating HCV infection and/or reducing the likelihood or severity of HCV infection in a subject in need thereof, which comprises administering to the subject the pharmaceutical composition of (a), (b), or (c) or the combination of (d) or (e).

(l) A compound of formula (I) for use in medicine, for use in prevention or treatment of HCV infection, or for use (i) in, (ii) as a medicament for, or (iii) in the preparation of a medicament for: (a) inhibiting HCV NS3 protease, or (b) treating HCV infection and/or reducing the likelihood or severity of HCV infection. In these uses, the compound of the present invention can optionally be employed in combination with one or more second therapeutic agents selected from HCV antiviral agents, anti-infective agents, and immunomodulators.

In all of these embodiments, the compound may optionally be used in the form of a pharmaceutically acceptable salt.

The term "or," as used herein, denotes alternatives that may, where appropriate, be combined. Thus, the term "or" includes each listed alternative separately as well as their combination if the combination is not mutually exclusive.

Reference to a compound also includes stable complexes of the compound such as a stable hydrate. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

II. Administration and Compositions

The term "administration" and variants thereof (e.g., "administering" a compound) means providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt and other agents.

The compound of the present invention may be administered in the form of pharmaceutically acceptable salts. The term "pharmaceutically acceptable salt" refers to a salt of the parent compound that has activity and that is not biologically or otherwise undesirable (e.g., is neither toxic nor otherwise deleterious to the recipient thereof). Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

As used herein, the term "prodrug" is intended to encompass an inactive drug form or compound that is converted into an active drug form or compound by the action of enzymes, chemicals or metabolic processes in the body of an individual to whom it is administered.

As used herein, the term "composition" is intended to encompass a product comprising the specified ingredients, as well as any product that results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" indicates a sufficient amount to exert a therapeutic or prophylactic effect. For a patient infected with HCV, an effective amount is sufficient to achieve one or more of the following effects: reduce the ability of HCV to replicate, reduce HCV load, and increase viral clearance. For a patient not infected with HCV, an effective amount is sufficient to achieve one or more of the following: a reduced susceptibility to HCV infection, and a reduced ability of the infecting virus to establish persistent infection for chronic disease.

For the purpose of inhibiting HCV NS3 protease and treating HCV infection and/or reducing the likelihood or severity of symptoms of HCV infection, the compound of the present invention, optionally in the form of a salt, can be administered by means that produces contact of the active agent with the agent's site of action. It can be administered by conventional means available for use in conjunction with pharmaceuticals, either as individual therapeutic agents or in a combination of therapeutic agents. It can be administered alone, but typically are administered with a pharmaceutical carrier selected on the basis of the chosen route of administration and standard pharmaceutical practice.

Compounds can, for example, be administered by one or more of the following routes: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further guidance for methods suitable for use in preparing pharmaceutical compositions of the present invention and of ingredients suitable for use in said compositions is provided in *Remington's Pharmaceutical Sciences*, 20$^{th}$ edition (ed. A. R. Gennaro, Mack Publishing Co., 2000).

The compound of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, 500, and 750 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

III. Combination Treatment

The quinoxaline macrocyclic compound described herein can be used in a combination treatment involving one or more additional therapeutic agents. Additional therapeutic agents include those also targeting HCV, targeting a different disease causing agent, or those enhancing the immune system. Agents enhancing the immune system include those generally enhancing an immune system function and those producing a specific immune response against HCV. Additional therapeutic agents targeting HCV include agents targeting NS3 and agents targeting other HCV activities such as NS5A and NS5B, and agents targeting host cell activities involved in HCV replication.

Different HCV inhibitors are described in different publications. Macrocyclic compounds useful as inhibitors the HCV protease inhibitors are described in WO 06/119061, WO 7/015785, WO 7/016441, WO 07/148,135, WO 08/051, 475, WO 08/051,477, WO 08/051,514, WO 08/057,209. Additional HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116, WO 02/48172, British Patent No. GB 2 337 262, and U.S. Pat. No. 6,323,180.

Additional examples of therapeutic agents that may be present in a combination include ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in WO 01/60379. The individual components of the combination can be administered separately at different times during the course of therapy or concurrently in divided or single combination forms.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compound of the present invention may also be administered in combination with an inhibitor of IMPDH, such as VX-497, which is disclosed in International Patent Application Publications WO 97/41211 and WO 01/00622; another IMPDH inhibitor, such as that disclosed in WO 00/25780; or mycophenolate mofetil. See A. C. Allison and E. M. Eugui, 44 (Suppl.) *Agents Action* 165 (1993).

For the treatment of HCV infection, the compound of the present invention may also be administered in combination with the antiviral agent amantadine (1-aminoadamantane). For a comprehensive description of this agent, see J. Kirschbaum, 12 *Anal. Profiles Drug Subs.* 1-36 (1983).

For the treatment of HCV infection, the compound of the present invention may also be administered in combination with the antiviral agent polymerase inhibitor R7128 (Roche).

The compound of the present invention may also be combined for the treatment of HCV infection with antiviral 2'-C-branched ribonucleosides disclosed in R. E. Harry-O'Kuru et al., 62 *J. Org. Chem.* 1754-59 (1997); M. S. Wolfe et al., 36 *Tet. Lett.* 7611-14 (1995); U.S. Pat. No. 3,480,613; and International Patent Application Publications WO 01/90121, WO 01/92282, WO 02/32920, WO 04/002999, WO 04/003000 and WO 04/002422; the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2, 6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compound of the present invention may also be combined for the treatment of HCV infection with other nucleosides having anti-HCV properties, such as those disclosed in International Patent Application Publications WO 02/51425, WO 01/79246, WO 02/32920, WO 02/48165 and WO 2005/003147 (including R1656, (2'R)-2'-deoxy-2'-fluoro-2'-C-methylcytidine, shown as compounds 3-6 on page 77); WO 01/68663; WO 99/43691; WO 02/18404 and WO 2006/021341, and U.S. Patent Application Publication US 2005/0038240, including 4'-azido nucleosides such as R1626, 4'-azidocytidine; U.S. Patent Application Publications US 2002/0019363, US 2003/0236216, US 2004/0006007 and US 2004/0063658; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compound of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. No. 6,777,392 and U.S. Patent Application Publication US 2004/0067901; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C,2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compound of the present invention may also be combined for the treatment of HCV infection with non-nucleoside inhibitors of HCV polymerase such as those disclosed in International Patent Application Publications WO 01/77091; WO 01/47883; WO 02/04425; WO 02/06246; WO 02/20497; WO 2005/016927 (in particular JTK003); and WO 2004/041201 (in particular HCV-796); the content of each is incorporated herein by reference in its entirety.

In one embodiment, non-nucleoside HCV NS5B polymerase inhibitors that are used in combination with the present HCV NS3 protease inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl- 6-oxo-6,7-dihydro-5H-indolo[1,2-d][1,4]benzodiazepine-10-carboxylic acid; and pharmaceutically acceptable salts thereof.

IV. Compound Evaluation

Compounds described herein can be evaluated for different activities such as the ability to inhibit HCV NS3 activity, HCV replicon activity, and HCV replication activity using techniques well-known in the art. (See, for example, Carroll et al., *J. Biol. Chem.* 278:11979-11984, 2003.)

One such assay is HCV NS3 protease time-resolved fluorescence (TRF) assay as described below and in Mao et al., *Anal. Biochem.* 373:1-8, 2008 and International Patent Application Publication WO 2006/102087. A NS3 protease assay can be performed, for example, in a final volume of 100 μl assay buffer containing 50 mM HEPES, pH 7.5, 150 mM NaCl, 15% glycerol, 0.15% TRITON X-100, 10 mM DTT, and 0.1% PEG 8000. NS3 and NS4A protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 μl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 μs delay. Testing concentrations of different enzyme forms are selected to result in a signal to background ratio (S/B) of 10-30. $IC_{50}$ values are derived using a standard four-parameter fit to the data. $K_i$ values are derived from $IC_{50}$ values using the following formula, $$IC_{50}=K_i(1+[S]/K_M),\qquad \text{Eqn (1),}$$

where [S] is the concentration of substrate peptide in the reaction and $K_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996); Mao et al., *Analytical Biochemistry* 373: 1-8, 2008.

V. General Compound Production

The present invention also includes processes for making the compound of formula (I). The compound of the present invention can be readily prepared according to the following reaction schemes and examples, or modifications thereof, using readily available starting materials, reagents and conventional synthesis procedures. In these reactions, it is also possible to make use of variants that are themselves known to those of ordinary skill in this art. Other methods for preparing the compound of the invention will be readily apparent to the person of ordinary skill in the art in light of the following reaction schemes and examples. Unless otherwise indicated, all variables are as defined above. The following reaction schemes and examples serve only to illustrate the invention and its practice.

Olefin metathesis catalysts include the following Ruthenium-based species: Scott J. Miller et al., *Application of Ring-Closing Metathesis to the Synthesis of Rigidified Amino Acids and Peptides,* 118 J. AM. CHEM. SOC. 9606 (1996); Jason S. Kingsbury et al., *A Recyclable Ru-Based Metathesis Catalyst,* 121 J. AM. CHEM. SOC. 791 (1999); Matthias Scholl et al., *Synthesis and Activity of a New Generation of Ruthenium-Based Olefin Metathesis Catalysts Coordinated with 1,3-Dimesityl-4,5-dihydroimidazol-2-ylidene Ligands,* 1(6) ORGANIC LETTERS 953 (1999); US 2002/0107138; Alois Fürstner et al., *Total Synthesis and Structural Refinement of the Cyclic Tripyrrole Pigment Nonylprodigiosin,* 64 J. ORG. CHEM. 8275 (1999). The utility of these catalysts in ring-closing metathesis is well known in the literature (e.g. Tina M. Trnka & Robert H. Grubbs, *The Development of $L_2X_2Ru=CHR$ Olefin Metathesis Catalysts: An Organometallic Success Story,* 34 ACC. CHEM. RES. 18 (2001)).

The following examples serve only to illustrate the invention and its practice. The examples are not to be construed as limitations on the scope or spirit of the invention.

LIST OF ABBREVIATIONS

List of Abbreviations
DCM/$CH_2Cl_2$ dichloromethane
DCE 1,2-dichloroethane
DIEA diisopropylethylamine
DMF dimethylformamide
DMSO dimethyl sulfoxide
Dppf diphenylphosphinoferrocene
$Et_2O$ diethyl ether
EtOAc ethyl acetate
HATU O-(7-azabenzotriazol-1-yl)-N,N,N',N'-tetramethyluronium hexafluorophosphate
HCl hydrochloric acid
TMSCl Chlorotrimethylsilane
TBAF Tetra-butyl ammonium fluoride
DMAP Dimethylamino pyridine
MeCN acetonitrile
MeOH methanol
Pd/C palladium on carbon
TBTU O-benzotriazol-1-yl-N,N,N',N'-tetramethyluronium tetrafluoroborate
TFA trifluoroacetatic acid
THF tetrahydrofuran
Flash Chromatography Purification using Biotage Horizon using silica gel cartridge and specified mobile phase gradient
HPLC Automated mass or UV triggered high performance liquid chromatography using acidified MeCN and $H_2O$ gradients as mobile phase
MHz Megahertz

SYNTHESIS OF INTERMEDIATES

Intermediates A

| Intermediate # | Structure | Name | Lit. Reference |
| --- | --- | --- | --- |
| A1 | 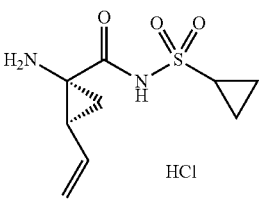 | (1R,2S)-1-Amino-N-(cyclopropylsulfonyl)-2-vinylcyclopropanecarboxamide hydrochloride | Wang et al., U.S. Pat. No. 6,995,174 |

Intermediate B1

3-methyl-N-({[(1R,2R)-2-pent-4-en-1-ylcyclopropyl]oxy}carbonyl)-L-valine

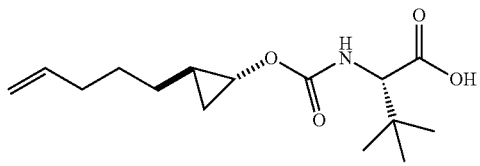

Step 1: [(1E)-hepta-1,6-dien-1-yloxy](trimethyl)silane

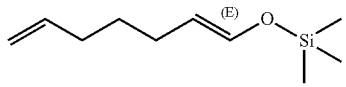

A solution (0.5 M) of butenyl magnesium bromide in THF (1.4 eq) was treated at −78° C. with Cu(I) Br.SMe$_2$ (0.05 eq) and HMPA (2.4 eq). The mixture was stirred for 10 min, then a solution (1 M) of acrolein (1 eq) and TMSCl (2 eq) in THF was added over 1 h such that the internal temperature remained below −68° C. The resulting mixture was stirred at −78° C. for 2 h, then treated with excess Et$_3$N and diluted with hexane. After reaching room temperature, the mixture was treated with a small portion of H$_2$O and filtered through CELITE. The filtrate was washed 10 times with H$_2$O and then with brine. The organic layer was dried, and the volatiles were removed to give a residue that was distilled under reduced pressure (20 mbar). The fraction collected at 80-86° C. contained the title compound (58%) as a colorless liquid. $^1$H NMR (400 MHz, CDCl$_3$) δ 6.19 (d, J=11.6 Hz, 1H), 5.85-5.75 (m, 1H), 5.02-4.92 (m, 3H), 2.08-2.02 (m, 2H), 1.94-1.88 (m, 2H), 1.46-1.38 (m, 2H), 0.18 (s, 9H).

Step 2: trans-2-pent-4-en-1-ylcyclopropanol

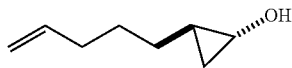

A solution (0.45 M) of the preceding compound in hexane was treated with a solution (15%) of Et$_2$Zn (1.2 eq) in toluene, and the resulting solution was cooled in an ice bath. Diiodomethane (1.2 eq) was added dropwise, then the solution was stirred for 1 h before being warmed to 20° C. Pyridine (6 eq) was added, and the slurry was stirred for 15 min then poured onto petroleum ether. The mixture was filtered repeatedly through CELITE until a transparent solution was obtained. This mixture was concentrated at 100 mbar, and the solution that remained (that contained trimethyl{[(trans)-2-pent-4-en-1-ylcyclopropyl]oxy}silane, toluene and pyridine) was further diluted with THF. The mixture was cooled to 0° C. then treated dropwise with a solution (1 M) of TBAF (1.2 eq) in THF. After 10 min, the mixture was allowed to warm to 20° C., and after a further 1 h was poured into H$_2$O. The aqueous phase was extracted with EtOAc, and the combined organic extracts were washed with brine then dried. Removal of the volatiles afforded a residue that was purified by flash chromatography (eluent 0-66% Et$_2$O/petroleum ether) to furnish the title compound (71%) as a colorless liquid. $^1$H NMR (400 MHz, CDCl$_3$) δ 5.85-5.75 (m, 1H), 5.00 (dd, J=17.1, 1.6 Hz, 1H), 4.94 (br d, J=10.4 Hz, 1H), 3.20 (apparent dt, J=6.4, 2.5 Hz, 1H), 2.10-2.04 (m, 2H), 1.52-1.44 (m, 2H), 1.29-1.19 (m, 1H), 1.15-1.07 (m, 1H), 0.95-0.87 (m, 1H), 0.71-0.66 (m, 1H), 0.31 (apparent q, J=6.0 Hz, 1H).

Step 3: methyl 3-methyl-N-(oxomethylene)-L-valinate

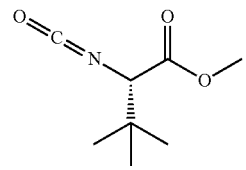

A solution (0.39 M) of methyl 3-methyl-L-valinate in a 2:1 mixture of saturated aqueous NaHCO$_3$ and CH$_2$Cl$_2$ was cooled in an ice bath and stirred rapidly. The mixture was treated with triphosgene (0.45 eq) in one portion, and the resulting mixture was stirred for 0.5 h. The reaction was diluted with CH$_2$Cl$_2$, and the layers were separated. The aqueous phase was extracted with CH$_2$Cl$_2$, then the combined organics were washed with brine and dried. Removal of the solvent gave the title compound as clear oil that was kept for 12 h under vacuum (0.1 mbar) then used directly in the subsequent step. $^1$H NMR (400 MHz, CDCl$_3$) δ 3.79 (s, 3H), 3.75 (s, 1H), 1.00 (s, 9H).

Step 4: methyl 3-methyl-N-({[(1R,2R)-2-pent-4-en-1-ylcyclopropyl]oxy}carbonyl)-L-valinate and methyl 3-methyl-N-({[(1S,2S)-2-pent-4-en-1-ylcyclopropyl]oxy}carbonyl)-L-valinate

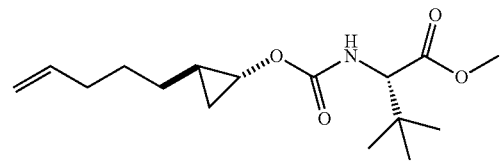

A solution (0.45 M) of trans-2-pent-4-en-1-ylcyclopropanol in toluene was treated with methyl 3-methyl-N-(oxomethylene)-L-valinate (1.1 eq) and then DMAP (1 eq). The resulting mixture was heated under reflux for 12 h then cooled to 20° C. H$_2$O and EtOAc were added, and the organic layer was separated and washed with 1N HCl, brine and dried. Removal of the volatiles afforded a residue that was purified twice by flash chromatography (eluent 0-30% Et$_2$O/petroleum ether). The first fractions contained methyl 3-methyl-N-({[(1R,2R)-2-pent-4-en-1-ylcyclopropyl]oxy}carbonyl)-L-valinate (38%) as an oil. MS (ES$^+$) m/z 298 (M+H)$^+$ The later fractions contained methyl 3-methyl-N-({[(1S,2S)-2-pent-4-en-1-ylcyclopropyl]oxy}carbonyl)-L-valinate (28%) as an oil. MS (ES+) m/z 298 (M+H)+

Step 5: 3-methyl-N-({[(1R,2R)-2-pent-4-en-1-ylcyclopropyl]oxy}carbonyl)-L-valine

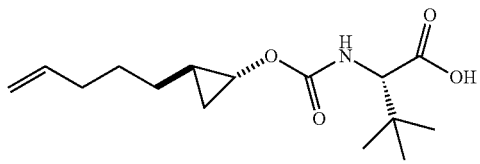

A solution (0.1 M) of methyl 3-methyl-N-({[(1R,2R)-2-pent-4-en-1-ylcyclopropyl]oxy}carbonyl)-L-valinate in 2:1 mixture of MeOH/H₂O was treated with LiOH.H₂O (4 eq) and then heated at 60° C. for 4 h. The mixture was cooled and concentrated to half volume, then diluted with EtOAc and acidified with aqueous HCl (1 N). The organic layer was separated and washed with brine then dried. Removal of the volatiles afforded the title compound (98%) as an oil. MS (ES+) m/z 284 (M+H)+

Intermediates C

Intermediate C1 methyl (4R)-4-[(3-chloro-7-methoxyquinoxalin-2-yl)oxy]-L-prolinate hydrochloride

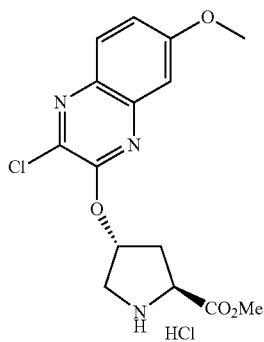

Step 1: 6-methoxyquinoxaline-2,3-diol

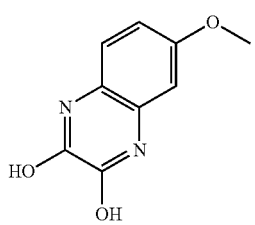

A suspension of 4-methoxybenzene-1,2-diamine dihydrochloride in diethyl oxalate (8 eq) was treated with Et₃N (2 eq) and then heated at 150° C. for 2 h. The mixture was cooled and filtered, and then the collected solid was washed with H₂O and EtOH. The residue was dried to give the title compound (69%). MS (ES+) m/z 193 (M+H)+

Step 2: 3-chloro-6-methoxyquinoxalin-2-ol

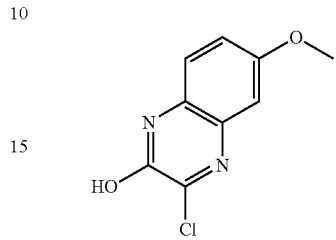

A solution (1.53 M) of 6-methoxyquinoxaline-2,3-diol in DMF was treated with SOCl₂ (1 eq) and heated at 110° C. After 1.5 h, the reaction mixture was cooled and poured into aqueous HCl (1 N). The resulting precipitate was filtered and washed with H₂O and Et₂O. The dried solid contained predominantly the title compound as a mixture with 6-methoxyquinoxaline-2,3-diol and 2,3-dichloro-6-methoxyquinoxaline. This material was used directly in the subsequent step. MS (ES+) m/z 211 (M+H)+

Step 3: 1-tert-butyl 2-methyl (2S,4R)-4-[(3-chloro-7-methoxyquinoxalin-2-yl)oxy]pyrrolidine-1,2-dicarboxylate

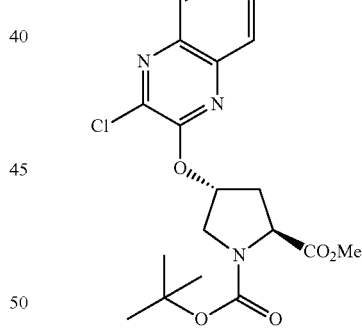

A solution (0.35 M) of 3-chloro-6-methoxyquinoxalin-2-ol in NMP was treated with Cs₂CO₃ (1.5 eq) and 1-tert-butyl 2-methyl (2S,4S)-4-{[(4-bromophenyl)sulfonyl]oxy}pyrrolidine-1,2-dicarboxylate (1.1 eq). The resulting mixture was stirred at 50° C. for 18 h, then a further portion (0.1 eq) of 1-tert-butyl 2-methyl (2S,4S)-4-{[(4-bromophenyl)sulfonyl]oxy}pyrrolidine-1,2-dicarboxylate was added. After stirring for 2 h, the mixture was cooled and diluted with H₂O and EtOAc. The organic phases were washed with aqueous HCl (1 N), saturated aqueous NaHCO₃ and brine. The dried organic phase was concentrated to a residue that was purified by flash-chromatography (0-60% EtOAc/petroleum ether) to give the title compound (35% for two steps) as a solid. MS (ES+) m/z 438 (M+H)+

Step 4: methyl (4R)-4-[(3-chloro-7-methoxyquinoxalin-2-yl)oxy]-L-prolinate hydrochloride

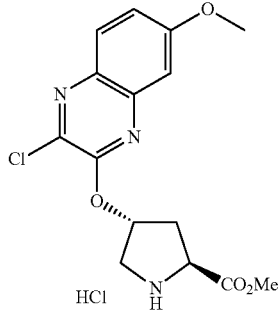

A solution (0.62 M) of 1-tert-butyl 2-methyl (2S,4R)-4-[(3-chloro-7-methoxyquinoxalin-2-yl)oxy]pyrrolidine-1,2-dicarboxylate in $CH_2Cl_2$ was treated with a solution (4 M) of HCl in dioxane (5 eq). The mixture was stirred at 20° C. for 2 h, then treated with a solution (4 M) of HCl in dioxane (2 eq). After 5 h, the reaction was judged complete and the mixture was concentrated under reduced pressure. The residue was triturated with $Et_2O$ to give the title compound (95%) as a solid. MS (ES$^+$) m/z 338 (M+H)$^+$

Example 1

Potassium {[(1R,2S)-1-({[(1aR,5S,8S,10R,22aR)-5-tert-butyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxalin-8-yl]carbonyl}amino)-2-vinylcyclopropyl]carbonyl}(cyclopropylsulfonyl)azanide

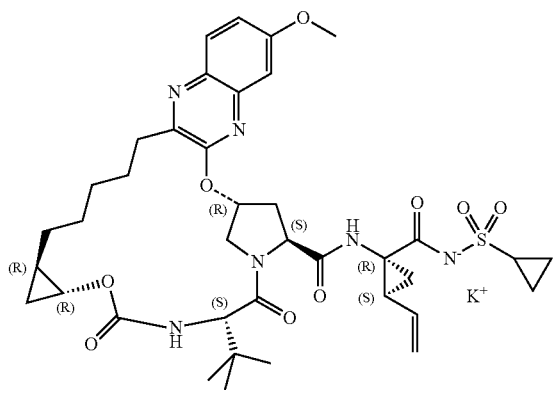

Step 1: methyl 3-methyl-N-({[(1R,2R)-2-pent-4-en-1-ylcyclopropyl]oxy}carbonyl)-L-valyl-(4R)-4-[(3-chloro-7-methoxyquinoxalin-2-yl)oxy]-L-prolinate

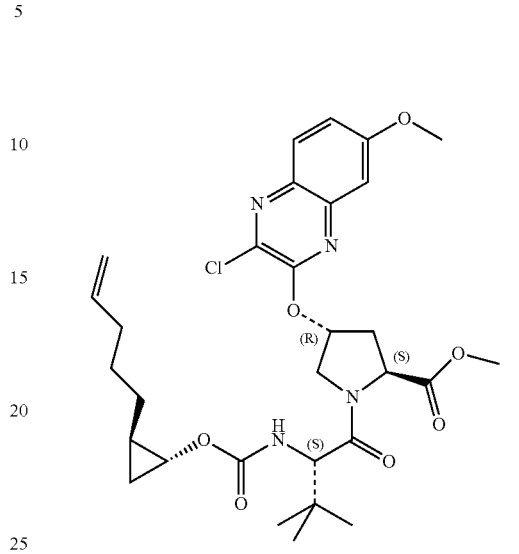

A solution (0.2 M) of methyl (4R)-4-[(3-chloro-7-methoxyquinoxalin-2-yl)oxy]-L-prolinate hydrochloride in DMF was treated with 3-methyl-N-({[(1R,2R)-2-pent-4-en-1-ylcyclopropyl]oxy}carbonyl)-L-valine (1.1 eq), DIEA (5 eq) and HATU (1.2 eq). The resulting mixture was stirred at 20° C. for 5 h, then diluted with EtOAc. The organic layer was separated and washed with aqueous HCl (1 N), saturated aqueous $NaHCO_3$ and brine. The dried organic phase was concentrated under reduced pressure to give a residue that was purified by flash chromatography (eluent 10-30% EtOAc/petroleum ether) to furnish the title compound (96%) as an oil. MS (ES$^+$) m/z 604 (M+H)$^+$

Step 2: methyl 3-methyl-N-({[(1R,2R)-2-pent-4-en-1-ylcyclopropyl]oxy}carbonyl)-L-valyl-(4R)-4-[(7-methoxy-3-vinylquinoxalin-2-yl)oxy]-L-prolinate

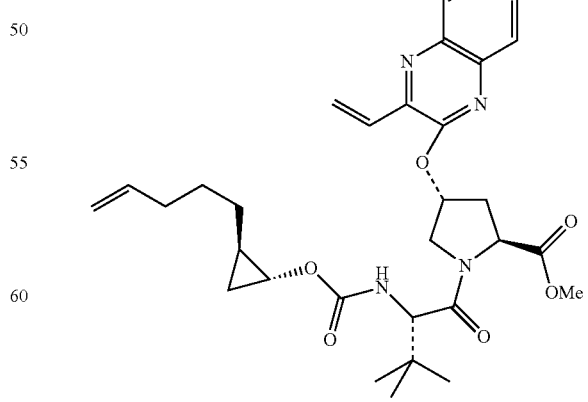

A solution (0.1 M) of methyl 3-methyl-N-({[(1R,2R)-2-pent-4-en-1-ylcyclopropyl]oxy}carbonyl)-L-valyl-(4R)-4-

[3-chloro-7-methoxyquinoxalin-2-yl)oxy]-L-prolinate in EtOH was treated with potassium trifluoro(vinyl)borate (1.5 eq) and triethylamine (1.5 eq). The resulting mixture was degassed, then PdCl$_2$(dppf)-CH$_2$Cl$_2$ adduct (0.1 eq) was added. The mixture was heated under reflux for 1 h, then cooled to room temperature and diluted with H$_2$O and EtOAc. The organic phase was separated, washed with H$_2$O and brine then dried. Removal of the volatiles afforded a residue that was purified by flash chromatography (20-30% EtOAc/petroleum ether) to give the title compound as a yellow foam that was used directly in the subsequent step. MS (ES$^+$) m/z 595 (M+H)$^+$ Step 3: methyl (1aR,5S,8S,10R,18E,22aR)-5-tert-butyl-14-methoxy-3,6-dioxo-1,1a,3,4,5,6,9,10,20,21,22,22a-dodecahydro-8H-7,10-methanocyclopropa[18,19][1,10,3,6]dioxadiazacyclononadecino[11,12-b]quinoxaline-8-carboxylate

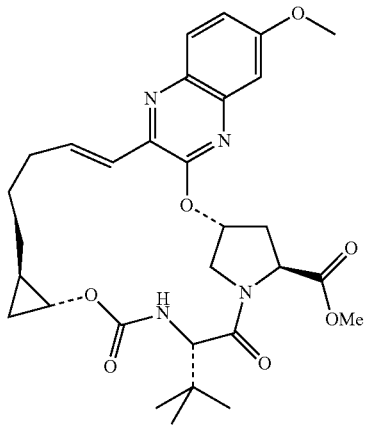

A solution (0.02 M) of methyl 3-methyl-N-({[(1R,2R)-2-pent-4-en-1-ylcyclopropyl]oxy}carbonyl)-L-valyl-(4R)-4-[(7-methoxy-3-vinylquinoxalin-2-yl)oxy]-L-prolinate in DCE was heated to 80° C. then treated with Zhan 1 catalyst (0.15 eq). The resulting mixture was stirred at 80° C. for 1 h, then cooled to room temperature and concentrated under reduced pressure. The residue was purified by flash chromatography (20-50% EtOAc/petroleum ether) to give the title compound (25% for 2 steps) as a foam. MS (ES$^+$) m/z 567 (M+H)$^+$ Step 4: methyl (1aR,5S,8S,10R,22aR)-5-tert-butyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxylate

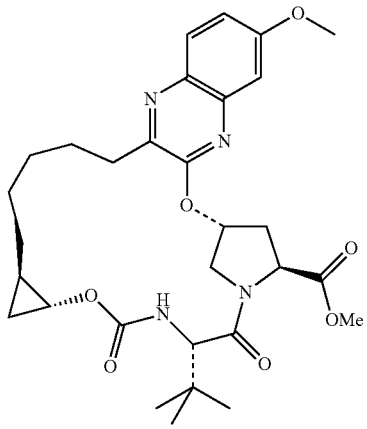

A solution (0.05 M) of methyl (1aR,5S,8S,10R,18E,22aR)-5-tert-butyl-14-methoxy-3,6-dioxo-1,1a,3,4,5,6,9,10,20,21,22,22a-dodecahydro-8H-7,10-methanocyclopropa[18,19][1,10,3,6]dioxadiazacyclononadecino[11,12-b]quinoxaline-8-carboxylate in MeOH/dioxane (1:1 ratio) was treated with Pd/C (8% in weight). The resulting mixture was stirred under atmosphere of hydrogen for 4 h. The catalyst was filtered off, and the filtrate was concentrated under reduced pressure to give the title compound (98%) as a solid. MS (ES$^+$) m/z 569 (M+H)$^+$ Step 5: (1aR,5S,8S,10R,22aR)-5-tert-butyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxylic acid

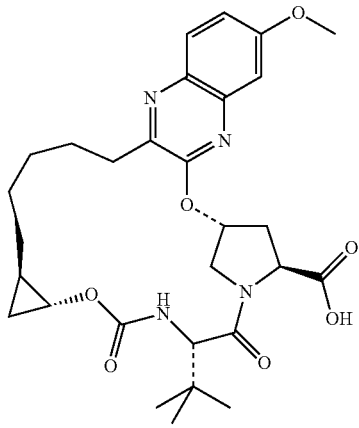

A solution (0.1 M) of methyl (1aR,5S,8S,10R,22aR)-5-tert-butyl-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxylate in a 1:1 mixture of H$_2$O/THF was treated with LiOH.H$_2$O (3 eq). The resulting mixture was stirred at 20° C. for 18 h, acidified with aqueous HCl (0.2 M) and diluted with EtOAc. The organic phase was separated, washed with aqueous HCl (0.2 M) and brine then dried. Removal of the volatiles afforded the title compound (98%) as a solid. MS (ES$^+$) m/z 555 (M+H)$^+$ Step 6: (1aR,5S,8S,10R,22aR)-5-tert-butyl-N-((1R, 2S)-1-{[(cyclopropylsulfonyl)amino]carbonyl}-2-vinylcyclopropyl)-14-methoxy-3,6-dioxo-1,1a,3,4,5, 6,9,10,18,19,20,21,22,22a-tetradecahydro-8H-7,10-methanocyclopropa[18,19][1,10,3,6] dioxadiazacyclononadecino[11,12-b]quinoxaline-8-carboxamide Step 7: potassium {[(1R,2S)-1-({[(1aR,5S,8S,10R, 22aR)-5-tert-butyl-14-methoxy-3,6-dioxo-1,1a,3,4,5, 6,9,10,18,19,20,21,22,22a-tetradecahydro-8H-7,10-methanocyclopropa[18,19][1,10,3,6] dioxadiazacyclononadecino[11,12-b]quinoxalin-8-yl]carbonyl}amino)-2-vinylcyclopropyl]carbonyl} (cyclopropylsulfonyl)azanide

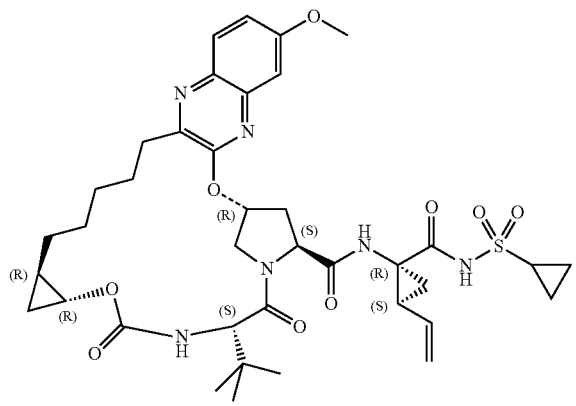
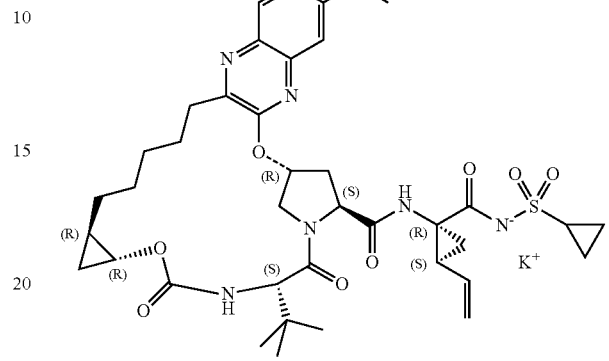

A solution (0.1 M) of (1aR,5S,8S,10R,22aR)-5-tert-butyl-14-methoxy-3,6-dioxo-1,1a,3,4,5,6,9,10,18,19,20,21,22, 22a-tetradecahydro-8H-7,10-methanocyclopropa[18,19][1, 10,3,6]dioxadiazacyclononadecino[11,12-b]quinoxaline-8-carboxylic acid in $CH_2Cl_2$ was treated with (1R,2S)-1-{[(cyclopropylsulfonyl)amino]carbonyl}-2-vinylcyclopropanaminium chloride (1.3 eq), DIEA (3 eq), DMAP (1.5 eq) and TBTU (1.45 eq). The resulting mixture was stirred at 20° C. for 18 h and then diluted with EtOAc. The solution was washed with aqueous HCl (0.2 M), saturated aqueous $NaHCO_3$ and brine. The organic phases were dried and concentrated to give a residue that was purified by flash-chromatography (eluent 2.5% $MeOH/CH_2Cl_2$) to give the title compound (89%) as a solid. $^{13}C$ NMR (100 MHz, DMSO-$d_6$) δ 172.32, 170.63, 169.04, 159.86, 156.95, 154.74, 148.10, 140.41, 133.55 (2 signals), 128.94, 118.21, 117.58, 105.89, 74.88, 59.75, 58.71, 55.68, 54.13, 54.01, 40.13, 34.49, 34.04, 33.76, 32.68, 30.71, 30.43, 28.55, 27.69, 27.28, 26.38, 21.98, 18.49, 10.67, 5.69, 5.46; MS (ES$^+$) m/z 767 (M+H)$^+$ The preceding material was taken up in EtOH and the resulting solution (0.025 M) was cooled to 0° C. A solution (0.02 M) of tert-BuOK (1.5 eq) in EtOH was added leading to the formation of a precipitate. The mixture was stirred at 20° C. for 18 h, then the solid was collected by filtration. This material was washed with EtOH and dried to give the title compound (93%) as a white crystalline solid. MS (ES$^+$) m/z 767 (M+H)$^+$ Example 2

Comparison of Different Compounds

The compound of Example 1 was compared to the compound of Examples 110 and 118 of WO 2008/057209. The results are shown in Tables 1 and 2 below. As illustrated in the tables and the discussion of the results, the compound of Formula (I) appears to have several advantageous properties compared to both the WO 2008/057209 Example 118 compound and the WO 2008/057209 Example 110 compound.

TABLE 1

| WO 2008/057209 Example 118 | Example 1 |
|---|---|
| Structure | |

TABLE 1-continued

| | | |
|---|---|---|
| NS 3/4A Inhibitory Activity[1] (Ki) 1b | <0.016 nM | <0.016 nM |
| Replicon Activity[2] $EC_{50}$ gt1b | 3 nM | 2 nM |
| Rat Plasma AUC @ 25mpk per os[3] | Not Available | 20.6 μM.h |
| Rat Liver Concentration @ 24 h (25 mpk per os)[3] | Not Available | 27.9 μM |
| Dog Plasma AUC @ 5mpk per os[3] | Not Available | 48.6 μM.h |
| Dog Liver Concentration @ 24 h (5mpk per os)[3] | Not Available | 120 μM |
| Covalent Protein Binding In Vivo[4] | Not Available | Rat @ 6 h plasma = LOQ, liver = LOQ |
| Physical properties[5] | Not Available | Potassium salt does not disproportionate in solution. |

WO 2008/057209
Example 110

Structure

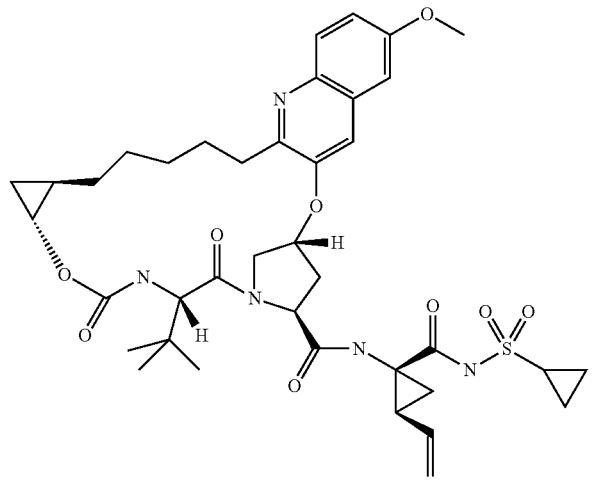

| | |
|---|---|
| NS 3/4A Inhibitory Activity[1] (Ki) 1b | <0.016 nM |
| Replicon Activity[2] $EC_{50}$ gt1b | 5 nM |
| Rat Plasma AUC @ 25mpk per os[3] | 5.8 μM.h |
| Rat Liver Concentration @ 24 h (25 mpk per os)[3] | 8.5 μM |
| Dog Plasma AUC @ 5mpk per os[3] | 1.0 μM.h |
| Dog Liver Concentration @ 24 h (5mpk per os)[3] | 3.3 μM |
| Covalent Protein Binding In Vivo[4] | Rat @ 6 h plasma = BLQ, liver = BLQ |
| Physical | Potassium salt |

TABLE 1-continued

| | |
|---|---|
| properties[5] | disproportionates to crystalline neutral form in solution |

Ki: Inhibition constant, reference to <0.016 nM indicates that the observed activity is less than 0.016 nM, the exact amount less than 0.016 nM was not determined by the assay;
EC50: Effective concentration achieving 50% viral replication suppression;
gt: Genotype;
AUC: Area Under the plasma concentration/time curve;
LOQ: Limit of quantitation (3 pmol/mg);
BLQ: Below limit of quantitation.

Formula (I) Compound Compared to WO 2008/057209 Example 110

Advantageous properties of the formula (I) compound versus the WO 2008/057209 Example 110 compound are the following:

1) Physical properties (no salt disproportionation for the Compound of formula (I));

2) Pharmacokinetic profile in rats following administration of the potassium salt; and 3) Liver (target organ) exposure.

The differences in properties are particularly advantageous for the formulation and administration of the formula (I) compound compared to the WO 2008/057209 Example 110 compound. The lack of salt disproportionation for the formula (I) compound enables dissolution of 1.8 mg/ml of the K+ salt form of the Compound of Example 1 in water. Although the K+ salt form of the WO 2008/057209 Example 110 compound has improved aqueous solubility (9.7 mg/mL), the compound thus dissolved disproportionates to give a crystalline zwitterionic form that has low aqueous solubility (<0.009 mg/ml). The lack of this behavior for the Compound of Example 1 provides an unexpected advantage in its formulation for pharmaceutical administration and results in improved pharmacokinetic properties as reported in Table 1 (plasma AUC and liver exposure for rat and dog). High plasma and liver exposure in preclinical species is advantageous for the selection of safe and efficacious doses for use in the treatment of patients.

Formula I Compound Compared to WO 2008/057209 Example 118

An observed advantage of the compound of formula (I) compared to WO2008/057209 Example 118 is its resistance profile against different mutant enzymes. In line with data from clinical studies with antiviral agents from related classes (e.g. HIV protease inhibitors), and also from studies with HCV NS3 protease inhibitors (e.g., VX-950, telaprevir) it is expected that viral resistance may develop in response to treatment with the current compounds. The compound of example 1 showed improved enzyme affinity (Ki) against different mutant enzymes that are known to confer resistance to HCV NS3 protease inhibitors. Table 2 summarizes activity against different mutant enzymes. Thus, an advantage of compound 1 may be an increased barrier to the development of resistant virus when administered to patients. It also provides the potential advantage to treat patients who have failed other therapies because of the development of resistance, since compound 1 may inhibit this resistant virus.

TABLE 2

Ki values[1] vs. 1b mutant enzyme (nM)

| 1b SHIFT | D168T | D168A | D168E | D168G | D168V | D168Y | D168Q |
|---|---|---|---|---|---|---|---|
| Example 1 | 0.18 | 0.43 | 0.04 | 0.08 | 0.14 | 0.22 | 0.12 |
| cmp 118 | 0.78 | 0.86 | 0.12 | 0.45 | 0.65 | 1.5 | 0.42 |

| 1b SHIFT | A156S | A156T | A156V | R155K | R155Q | R155G | R155N |
|---|---|---|---|---|---|---|---|
| Example 1 | 0.05 | 5.2 | 11 | 0.07 | 0.43 | 0.63 | 0.13 |
| cmp 118 | 0.10 | 3.4 | 15 | 0.08 | 1.9 | 2.3 | 0.56 |

[1]Comparative data collected in the same run of the enzyme assays

Further expected advantageous properties of the formula (I) compound versus the WO 2008/057209 Example 110 compound include the following:

1) Low in vivo covalent binding; and
2) High plasma and liver exposure.

The formula (I) compound was found to have very good covalent binding in vivo characteristics and pharmacokinetic properties. Based on observed covalent binding in vivo and pharmacokinetic properties of the Example 1 compound, and work done in testing other compounds, it is expected that the formula (I) compound has significantly better in vivo covalent binding characteristics and pharmacokinetic properties than the WO 2008/057209 Example 118 compound.

Compounds that covalently bind to proteins, or that form metabolites that subsequently become covalently bound to proteins, potentially give rise to adverse events in patients such as immunological toxicities mediated by antibody responses to the drug-protein conjugate, and other idiosyncratic toxicities. (See Chem. Res. Toxicol. 2004, 17, 3-16.)

The compound of Example 1 showed undetectable binding to plasma proteins following oral administration of a single 20 mg/kg dose to rats. (See Table 1.) It is expected that, under analogous conditions, the WO 2008/057209 Example 118 compound would demonstrate detectable binding to rat plasma and liver proteins, and therefore may be considered a less advantageous compound for administration to human subjects than the compound of formula (I).

The expectation concerning WO 2008/057209 Example 118 binding is supported by in vivo covalent binding data observed for related compounds from WO 2008/057209 that contain the (R,R)-trans-2-alkylcyclopentanol moiety incorporated in Example 118. The data is summarized in Table 3.

TABLE 3

| WO 2008/057209 Example 108 | WO 2008/057209 Example 103 |
|---|---|
| Structure | Structure |
| Covalent Protein Binding In Vivo[4] | Rat @ 6 h<br>plasma = 15 pmol eq./mg<br>liver = 38 pmol eq./mg | Rat @ 6 h<br>plasma = 6 pmol eq./mg<br>liver = 24 pmol eq./mg |

| WO 2008/057209 Example 96 |
|---|
| Structure |
| Covalent Protein Binding In Vivo[4] — Rat @ 6 h, plasma = 6 pmol eq./mg, liver = 63 pmol eq./mg |

It is advantageous to have high plasma and liver exposure in preclinical species to effectively demonstrate that the potential drug candidate does not elicit undesired toxicities. It is also more likely that a compound that has high liver and plasma exposure in animals displays the same behavior in man than one that does not. For such a compound the required efficacious exposure in man can be reached with a lower dose, advantageous both for the cost and ease of manufacturing the drug, but also potentially lowering the likelihood of adverse effects. Target organ exposure in multiple preclinical species provides a rationale that high target organ exposure is achievable for the compound in patients, and high liver exposure in both rat and dog allows for confident evaluation of preclinical toxicity. High liver exposure is especially advantageous for HCV since this is the target organ for the drug.

The compound of Example 1 had a very good rat plasma and liver exposure. The observed rat plasma and liver exposure was at a level greater than expected for other compounds in WO 2008/057209. The expectation is based on testing several different compounds from WO 2008/057209 by oral administration to both rat (25 mpk) and dog (5 mpk). Thus, the compound of formula (I) is expected to have rat and dog plasma and liver exposures greater than the WO 2008/057209 compound 118.

Methods

NS 3/4A Inhibitory Activity[1] (Ki): NS 3/4A Inhibitory Activity was determined as described in Section IV. Compound Evaluation supra., and Mao et al., *Anal Biochem* 373: 1-8, 2008.

Replicon Activity[2] $EC_{50}$: Replicon Activity was determined using the procedures described in Carroll et al., *J. Biol. Chem.* 278:11979-11984, 2003 and Olsen et al., *Anti Microb. Agents* 48:3944-3953, 2004.

Rat Plasma AUC @25 mpk per os[3]: Test compounds were dissolved in a suitable dosing vehicle for iv administration (e.g. 20%:60%:20% DMSO:PEG400:Water) or per os administration (e.g., 10% POLYSORBATE80: 90% Water or 100% PEG400) Animals were administered (n=3) using a crossover study design for non-rodents. Plasma samples were collected at time points between 2 minutes and 24 h, and compound levels were determined by RP-HPLC. Liver samples were collected post mortem in rat and following anesthesia (0.5 h prior to biopsy) in dog. Liver samples were weighed, homogenized, and diluted using techniques known to those skilled in the art, and compound levels were determined by RP-HPLC.

Pharmacokinetic parameters were calculated based on non-compartmental analysis (e.g., using WATSON®, WINNO-LIN®). Predose concentrations that were below the limit of quantitation (BLQ) were assigned a value of 0. For oral AUC estimation, the first BLQ value in the terminal phase were given a value equal to ½ Lowest Limit Of Quantitation, while subsequent values in the terminal phase were assigned a value of 0, Standard pharmacokinetic parameters CLp, Vdss, half-life (only for IV), % F, $C_{max}$, $T_{max}$, $AUC_{0-last}$, $AUC_{0-infinity}$ were calculated. AUC values were calculated using linear trapezoidal method for ascending concentrations and the log trapezoidal method for descending concentrations.

In-Vivo Covalent Binding[4]: Test compounds were suitably radiolabeled (3H) and a 20 mg/kg dose containing 25-75 mCi/rat (purity>98.5%) radioactivity was prepared by combination of the cold compound and evaporated radiotracer stock solution. This mixture was dissolved in a dosing vehicle suitable for per os administration (see above) then administered orally to rat (n=3 per timepoint, 2 h, 6 h, 24 h). Plasma and liver were collected and flash frozen/stored at −80° C. before analysis.

Counting of the plasma samples: Place a 200 µL aliquot in a 20 mL scintillation vial. Add 500 µL of SOLVABLE™ and incubate at 1 h with shaking at 55° C. Remove, allow to cool prior to the addition of 15 mL scintillation cocktail, and count. Plasma samples (200 aliquot) were then processed as described below for liver proteins.

Tissue homogenization: Weighed liver samples were diluted with 2 vol 100 mM phosphate buffer (pH 7.4) and homogenized on ice.

Counting of the liver homogenate: Aliquots were placed in a 20 mL scintillation vial, diluted with 1 mL of SOLVABLE™ and incubated for 1 h with shaking at 55° C. After removal from the incubator and cooling 15 mL scintillation cocktail and 30% $H_2O_2$ were added and the radioactivity counted.

Protein precipitation: Take 500 µL aliquot, add 1:8 homogenate:acetonitrile (if compound is suspected to have low solubility in acetonitrile, another solvent may be selected), vortex and centrifuge (3500 rcf for 20 min) Discard the supernatant.

Protein precipitate resuspension: Sonication (minimal intensity, <5 sec) and vortexing until the pellet crumbles in 80% MeOH:20% water.

Wash of the protein pellet: 2-5 mL 80:20 MeOH:water. If needed, remove 1.0 mL of the supernatant, add 15 mL of scintillation cocktail and count. Continue to wash the protein pellet until radioactivity in supernatant is <200 DPM or DPMs cease to decrease by more than 200 in consecutive washes.

Dissolution of the final pellet: 1 mL of 1 N NaOH or Solvable™, incubated at 50° C. overnight or until completely dissolved.

Counting of the final pellet: 1 mL of dissolved pellet, 15 mL scintillation cocktail (if another scintillation cocktail other than ULTIMA GOLD™ is used, pellet may require neutralization using 1 N HCl), and count.

Protein concentration of the final pellet: BCA or BIO-RAD kit using BSA as a standard.

Counting blank samples: 15 mL scintillation cocktail, in duplicate.

Counting of the dosing solution: count a known volume of the dosing solution in triplicate.

Data Analysis: Average the radioactivity counts (DPM) of the dosing solution and calculate the specific activity of the dosing solution in µCi/mol. Average the radioactivity counts of the blank samples. Subtract the counts of the averaged blank sample from the counts obtained from each liver and plasma pellet. Calculate the amount of radioactivity (µCi) per unit volume (L) for each liver and plasma pellet. Calculate the concentration of radioactivity in each plasma and liver pellet by dividing the value obtained above (µCi/L) by the specific activity (µCi/mol). Calculate the amount of covalently bound radioactivity to protein in pmol/mg protein.

Counting blank samples: 15 mL scintillation cocktail, in duplicate.

Counting of the dosing solution: count a known volume of the dosing solution in triplicate.

Physical properties[5]: The crystalline test compounds (potassium salt, ca. 5 mg) was weighed in a glass vial and water or aqueous buffer was added (100 µL). The slurry obtained was stirred for 24 h at room temperature. After centrifuging, the supernatant was analyzed by reversed-phase HPLC and the equilibrium solubility determined by comparison with a calibration curve. The solid material was in part transferred onto an XRPD plate, dried and then analyzed by X-Ray Powder Diffraction. The XRPD pattern was compared with positive controls for crystalline K+ salt, crystalline zwitterionic (or acidic) and amorphous forms of the test compound. A further determination of the salt form was obtained from a second portion of the solid material that was analyzed by 400 MHz NMR (Bruker) following dissolution in DMSO-$d_6$. 1H-NMR spectra were compared to positive controls described above.

None of the references described throughout the present application are admitted to be prior art to the claimed invention.

Other embodiments are within the following claims. While several embodiments have been shown and described, various modifications may be made without departing from the spirit and scope of the present invention.

What is claimed is:

1. A method of preparing a compound of formula (I):

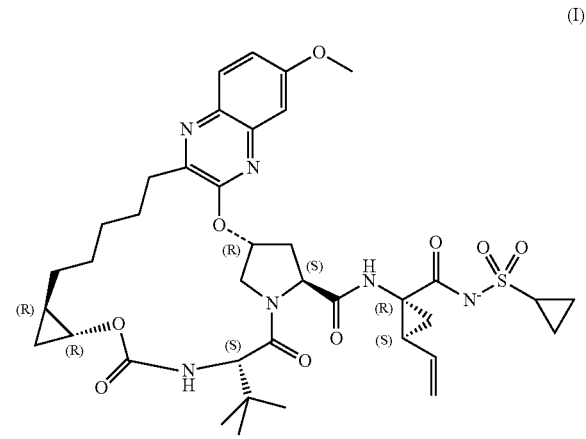

said method comprising:
  reacting (1aR,5S,8S,10R,22aR)-5-tert-butyl-14-methoxy-3,6-dioxo-1,1a,3,4,5,6,9,10,18,19,20,21,22,22a- tetradecahydro-8H-7,10-methanocyclopropa[18,19][1,10,3,6]dioxadiazacyclononadecino[11,12-b]quinoxaline-8-carboxylic acid

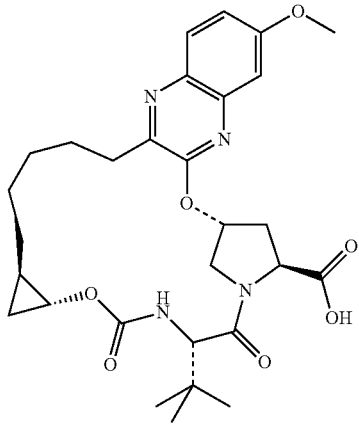

with (1R,2S)-1-Amino-N-(cyclopropylsulfonyl)-2-vinyl-cyclopropanecarboxamide hydrochloride

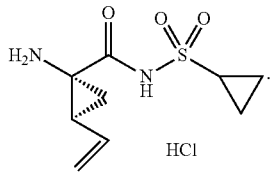

2. The method of claim 1, wherein the reacting is conducted in the presence of at least one reagent selected from the group consisting of diisopropylethylamine (DIEA), dimethylamino pyridine (DMAP) and O-benzotriazol-1-yl-N,N,N',N'-tetramethyluronium tetrafluoroborate (TBTU).

3. The method of claim 1, wherein the reacting is conducted in the presence of diisopropylethylamine (DIEA), dimethylamino pyridine (DMAP) and O-benzotriazol-1-yl-N,N,N',N'-tetramethyluronium tetrafluoroborate (TBTU).

4. A method of preparing a pharmaceutically acceptable salt of a compound of formula (I):

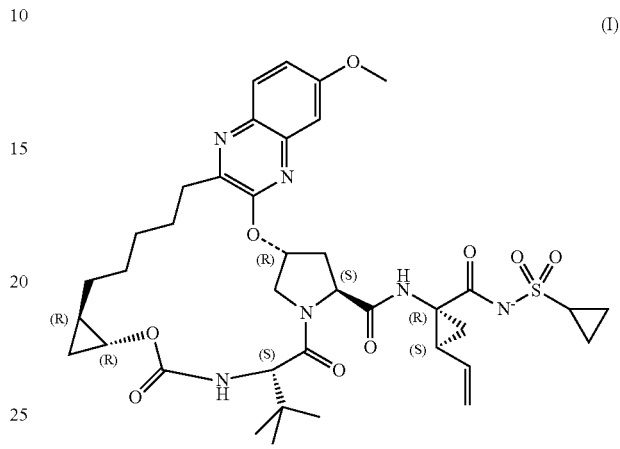

said method comprising:
reacting a compound of formula (I) with a metal alkoxide to form a salt or the compound of formula (I).

5. The method of claim 4, wherein the metal alkoxide is a potassium alkoxide.

6. The method of claim 5, wherein the potassium alkoxide is a potassium tert-butoxide.

7. A compound prepared by the method of claim 1.

8. A compound prepared by the method of claim 4.

* * * * *